United States Patent [19]

Machida et al.

[11] Patent Number: 4,867,169

[45] Date of Patent: Sep. 19, 1989

[54] ATTACHMENT ATTACHED TO ULTRASOUND PROBE FOR CLINICAL APPLICATION

[76] Inventors: Kaoru Machida, 404 Horan-Sumiyoshi-Residence, 1-1-39, Murasakizuka, Ootawara-shi, Tochigi-ken; Akifumi Suzuki, 101 Daiichi-Sanwa-Corpo, 5-17, Minami-cho, Nishinasunomachi, Nasu-gun, Tochigi-ken; Masayuki Takano, 2-307, Koyosokushinjutaku, 3-3722-51, Asaka-cho, Ootawara-shi, Tochigi-ken; Yushichi Kikuchi, 4-139-119, Minamigoya, Nishinasunomachi, Nasu-gun, Tochigi-ken, all of Japan

[21] Appl. No.: 70,590

[22] Filed: Jul. 7, 1987

[30] Foreign Application Priority Data

Jul. 29, 1986 [JP] Japan ................................. 61-179188
Jul. 29, 1986 [JP] Japan ................................. 61-179189

[51] Int. Cl.$^4$ .............................................. A61B 8/00
[52] U.S. Cl. ............................ 128/662.03; 128/662.03; 128/660.1
[58] Field of Search ...................... 128/660, 660.10; 73/624, 625, 627, 628, 632, 644, 662.03, 618

[56] References Cited

U.S. PATENT DOCUMENTS

| | | | |
|---|---|---|---|
| 4,181,120 | 1/1980 | Kunii et al. | 128/660 |
| 4,418,698 | 12/1983 | Dory | 73/618 |
| 4,579,123 | 4/1986 | Chen et al. | 128/660 |
| 4,612,809 | 9/1986 | Cribbs et al. | 73/644 |
| 4,688,578 | 8/1987 | Takano et al. | 128/660 |
| 4,787,070 | 11/1988 | Suzuki et al. | 128/660.1 |

*Primary Examiner*—Francis Jaworski
*Assistant Examiner*—George Manuel

[57] ABSTRACT

In the present invention, an attachment which is attached to an ultrasound probe for clinical application is as follows. When the attachment is brought into contact with a skin surface of a body, the ultrasound probe radiates ultrasound beams toward the body which is scanned with ultrasound beams in a first plane. The attachment comprises a reservoir section for holding an acoustic medium, an attachment section for attaching the attachment to the ultrasound probe, and a contact membrane arranged opposite to the attachment section to be brought into contact with the skin surface. The dimension of the contact membrane is smaller than that of the attachment section when the reservoir section is cut at a plane perpendicular to the first plane. The reservoir section is formed without causing the reservoir section to shield the ultrasound beams which are converged by the convergence means. Thus, when an operator moves the ultrasound probe, the frictional force between the contact membrane and the skin surface is small. When the attachment is pivoted while being brought into contact with the skin surface, the attachment can be easily fitted on the human body. Therefore, the operability of the attachment and the contact between the contact membrane and the skin surface can be improved without causing the reservoir section to shield the converged ultrasound beams. Also, in this invention, the contact membrane projects outwardly when the attachment is cut at the first plane and has a predetermined radius of curvature. For this reason, the transmittance of the ultrasound beams transmitted through the contact membrane is improved, and the ultrasound beams multiple-reflected by the contact membrane can be eliminated.

7 Claims, 6 Drawing Sheets

ATTACHMENT ATTACHED TO ULTRASOUND PROBE FOR CLINICAL APPLICATION

BACKGROUND OF THE INVENTION

The present invention relates to an attachment attached to an ultrasound probe for clinical application.

An ultrasound probe comprises a transducer array having a plurality of transducer elements aligned in a single direction. Ultrasound beams are radiated from the transducer elements toward a human body and are deflected therein in a predetermined direction, thereby scanning the human body. For example, in a sector scan method, the ultrasound beams are deflected in a fan shape, while in a linear scan method, the supersound beams are deflected in directions parallel to each other. Ultrasound beams reflected by the interior of the human body are received by the transducer elements. The received ultrasound beams are converted to eletrical signals. Then, a tomographic image of the human body is displayed on a cathode-ray tube in correspondence with the electrical signals. In order to sequentially diagnose tomographic images of the human body, an operator moves the ultrasound probe in a direction perpendicular to the deflecting direction of the ultrasound beams.

When an organ which is near the surface of the patient's skin is to be diagnosed, an attachment incorporating an acoustic medium is often attached to the ultrasound probe. FIGS. 1 to 3 show this attachment. Attachment 2 comprises resin casing 3 storing an acoustic medium, and attachment section 4 for attaching the casing 3 to probe 1. Contact membrane 5 formed of silicone rubber is provided to the distal end portion of casing 3.

As shown in FIGS. 1 and 2, casing 2 normally has a cubic shape. More specifically, surface 6, parallel to the deflecting direction of the ultrasound beams, has a rectangular shape, as shown in FIG. 1. Surface 7, perpendicular to the deflecting direction of the ultrasound beams, has also a rectangular shape. For this purpose, contact membrane 5 has relatively large width W. When the operator moves the ultrasound probe, frictional resistance between the skin surface and the contact membrane of the attachment is increased. For this reason, when the operator moves the probe along the skin surface, the attachment has poor operability. When the attachment is turned while being brought into contact with the skin surface, the attachment cannot be satisfactorily contact with the human body. Therefore, the contact between the membrane of the attachment and the skin surface is degraded.

As shown in FIGS. 1 to 3, the attachment has a flat contact membrane. For this reason, as indicated by the arrow in FIG. 3, the ultrasound beams are reflected by the inner surface of the contact membrane 5, are multiple-reflected by the inner surface of casing 3, and are then received by the transducer elements. In this case, a multiple-reflected image is displayed on the cathode-ray tube, thus hindering a precise diagnosis (reading). When the contact membrane is flat, if a neck (for example) is to be diagnosed, contact between the membrane and the skin surface is degraded.

The attachment may comprise a flexible water bag. In this case, when the water bag is brought into contact with the skin surface, since its contact membrane is flat, a multiple-reflected image is displayed on a cathode-ray tube, and a precise diagnosis (reading) cannot be performed.

SUMMARY OF THE INVENTION

It is an object of the present invention to provide an attachment attached to an ultrasound probe for clinical application, which can improve operability and contact with a skin surface, and can prevent a multiple-reflected image from being displayed on a cathode-ray tube, whereby precise diagnosis can be performed.

According to the present invention, an attachment attached to a diagnostic ultrasound probe has the following structure. When the attachment is brought into contact with a skin surface of a body, the ultrasound probe radiates ultrasound beams toward the body that is scanned with ultrasound beams along a first plane. The ultrasound probe has a convergence means which causes the ultrasound beams to converge on a point in the first plane. The attachment comprises a reservoir section for holding an acoustic medium, an attachment section for attaching the reservoir section to the ultrasound probe, and a contact membrane arranged opposite to the attachment section to be brought into contact with the skin surface. The dimension of the contact membrane is smaller than that of the attachment section when the reservoir section is cut at a plane perpendicular to the first direction. The reservoir section is formed without causing the reservoir section to shield the ultrasound beams which are converged by the convergence means.

As described above, the dimension of the contact membrane can be smaller than a conventional one. When the operator moves the ultrasound probe, the frictional force between the contact membrane and the skin surface is small. Therefore, the operability of the attachment can be improved without causing the reservoir section to shield the converged ultrasound beams. When the contact membrane is pivoted while being brought into contact with the skin surface (pivot scanning), the attachment can be easily fitted on the human body. For this reason, contact between the contact membrane and the skin surface can be improved without causing the reservoir section to shield the converged ultrasound beams.

According to the present invention, the contact membrane is convex do as to projects outwardly from the reservoir section when the attachment is cut at the first plane and has a predetermined radius of curvature. For this reason, the transmittance of the ultrasound beams transmitted through the contact membrane is improved, and the ultrasound beams multiple-reflected by the contact membrane toward the first and second surfaces can be eliminated. The ultrasound beams can be prevented from being undesirably reflected by the interior of the reservoir section. Therefore, a multiple-reflected image will not be displayed on the cathode-ray tube, and a precise diagnosis will not be impeded.

BRIEF DESCRIPTION OF THE DRAWINGS

FIGS. 1 to 3 are views showing the prior art of the present invention, in which

FIG. 1 is a view showing an attachment attached to an ultrasound probe for clinical application when viewed from a y direction, FIG. 2 is a view showing the attachment shown in FIG. 1 when viewed from an x direction, and FIG. 3 is a view including a partially cutaway section of the attachment shown in FIG. 1 when the attachment is viewed from the y direction; and FIGS. 4 to 11 are views showing an attachment attached to an ultrasound probe for clinical application according to the present invention, in which FIG. 4 is a perspective view of the attachment, FIG. 5 is a view showing the attachment shown in FIG. 4 when viewed from the y direction, FIG. 6 is a view showing the attachment shown in FIG. 4 when viewed from the x direction, FIG. 7 is a sectional view of the attachment shown in FIG. 4 taken along the x direction, FIG. 8 is a sectional view of the attachment shown in FIG. 4 taken along the y direction, FIGS. 9 and 10 are views showing the operation of the attachment according to the present invention, in which FIG. 9 is a view when tomographic images of a human body are sequentially imaged, and FIG. 10 is a view when they are pivot-scanned, FIG. 11 is a view of a cathode-ray tube on which the tomographic image is displayed.

DETAILED DESCRIPTION OF THE PREFERRED EMBODIMENT

Figure 4:
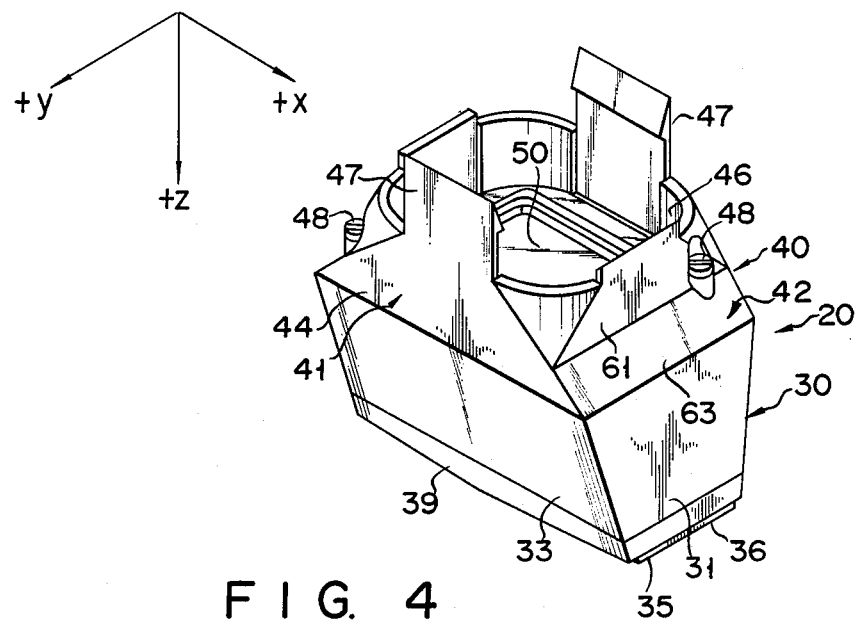

FIG. 4 shows an attachment attached to an ultrasound probe for clinical application. For the sake of simplicity, x, y, and z directions are defined as shown in FIG. 4. In addition, the +z direction is defined as an upward direction, and the −z direction is defined as a downward direction.

Figure 7:
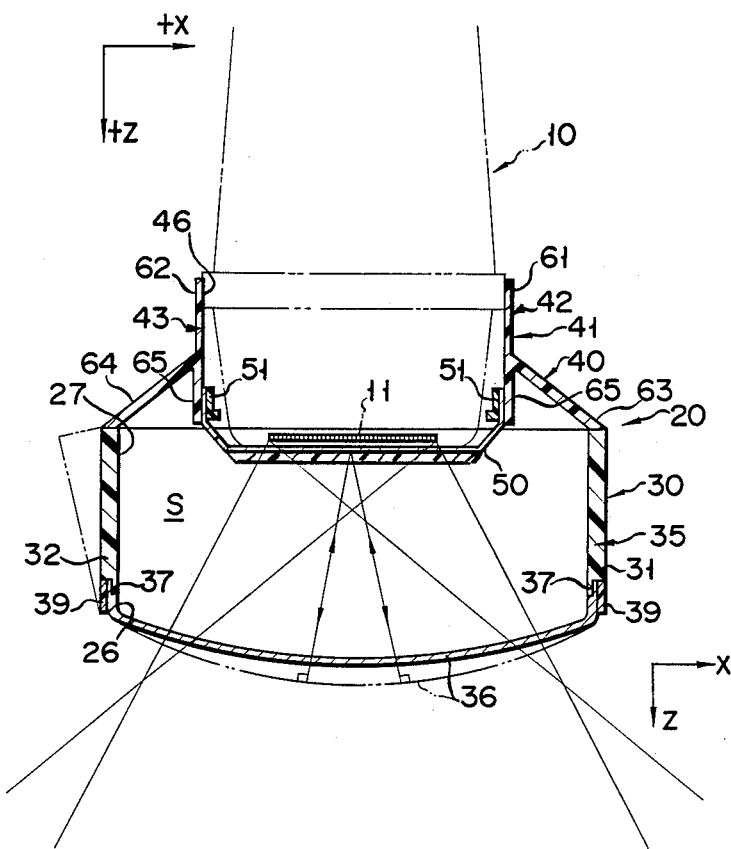
Figure 11:
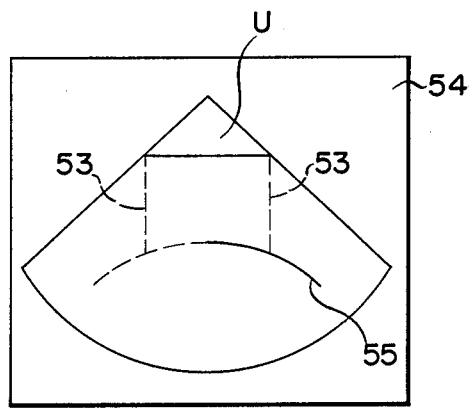

An ultrasound probe for clinical application will be briefly described. As shown in FIG. 7, ultrasound probe 10 comprises a plurality of transducer elements 11 aligned in the ±x directions. Ultrasound beams are radiated from transducer elements 11 in the +z direction toward a human body, and the human body is scanned by the ultrasound beams deflected in the ±x directions. More specifically, in the sector scan method, as shown in FIG. 7, the ultrasound beams are generated and deflected in an apparent fan shape. The ultrasound beams reflected by the interior of the human body are received by transducer elements 11. The body is scanned with the ultrasound beams along a plane including the x and z axes. The received ultrasound beams are converted to electrical signals, and a tomographic image is displayed on cathode-ray tube 54 in correspondence with the electrical signals, as shown in FIG. 11. In order to sequentially diagnose the tomographic images of the human body, the operator moves ultrasound probe 10 in the ±y directions.

As shown in FIG. 4, attachment 20 comprises reservoir section 30 for storing an acoustic medium and attachment section 40 for attaching reservoir section 30 to ultrasound probe 10. Reservoir section 30 has first and second surfaces 31 and 32 perpendicular to the x direction. First and second surfaces 31 and 32 have a trapezoidal shape when viewed from the x direction. Reservoir section 30 has third and fourth surfaces 33 and 34 (not shown in FIG. 4) for coupling first and second surfaces 31 and 32, respectively. Third and fourth surfaces 33 and 34 are tapered toward the +z direction. Therefore, a distance between the lower edges of third and fourth surfaces 33 and 34 in the y direction is smaller than a distance between the upper edges of thereof in the y direction. As is shown in FIG. 7, first to fourth surfaces 31 to 34 define first tapered rectilinear member 35. The lower edges of first to fourth surfaces 31 to 34 define first opening 26 open in the +z direction. The upper edges of first to fourth surfaces 31 to 34 define second opening 27 open in the −z direction.

Figure 5:
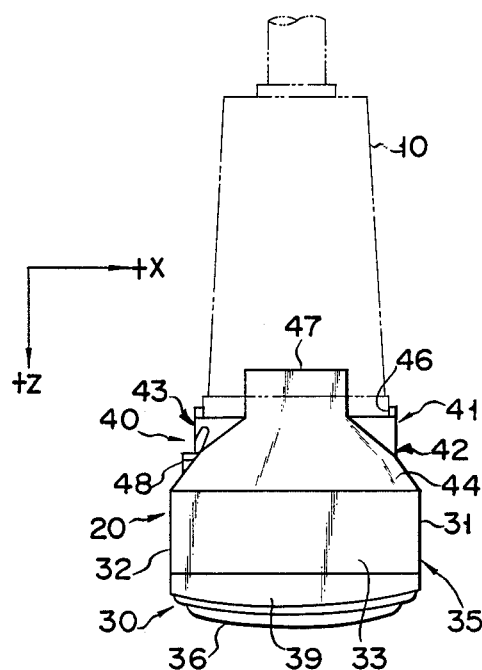
Figure 6:
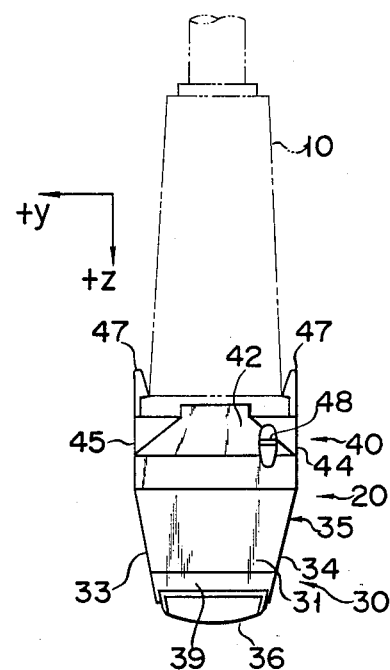

As shown in FIG. 7, contact membrane 36 formed of flexible silicone rubber is mounted on the lower end of first rectilinear member 35. More specifically, flanges 37 and 38 (shown in FIG. 8) are formed at the lower ends of first cylindrical member 35. The end portions of contact membrane 36 are laid on the outer surfaces of flanges 37 and 38 and are adhered thereto. Ring member 39 is engaged with the outer surface of the end portion of contact membrane 36 and is adhered thereto. In this case, as is shown in FIG. 5, the lower ends of third and fourth surfaces 33 and 34 have an arcuated shape so as to have a convex lower surface. Contact membrane 36 is formed to be convex in correspondence with the arcuate shape of flange 38, as shown in FIG. 7. The reason why contact membrane 36 is convex will be explained later.

Figure 8:
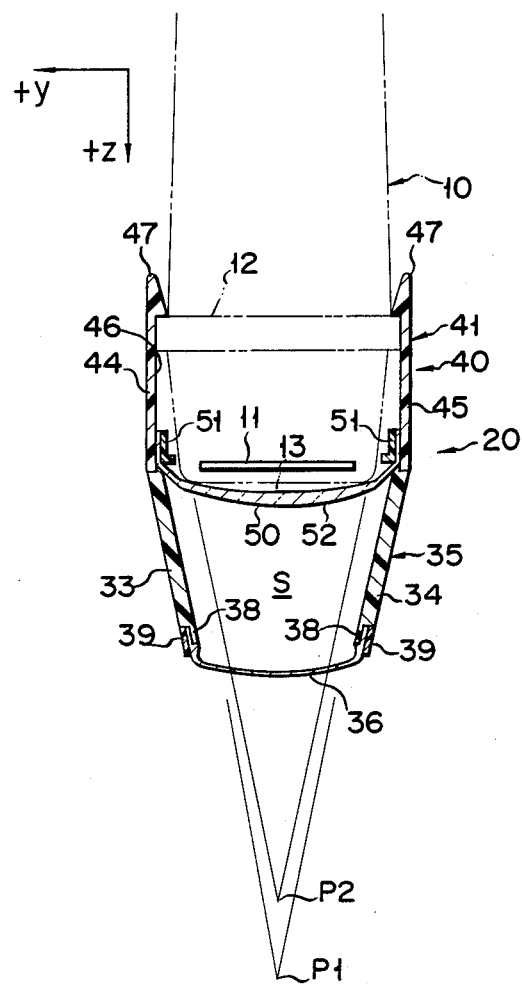

As is shown in FIGS. 7 and 8, attachment section 40 comprises fifth and sixth surfaces 42 and 43, respectively, having planes 61 and 62 perpendicular to the ±x directions and inclined planes 63 and 64, and seventh and eighth surfaces 44 and 45 perpendicular to ±y directions. Flanges 65 are formed on the interior of fifth and sixth surfaces 42 and 43. Fifth to eighth surfaces 42 to 45 define second rectilinear member 41. The upper end portion of rectilinear member 41 defines opening 46. Ultrasound probe 10 is inserted in rectilinear member 41 through opening 46. Clips 47 extending in the −z direction are formed on seventh and eighth surfaces 44 and 45, respectively. Clips 47 are fitted on stepped portions 12 of ultrasound probe 10, when probe 10 is attached to section 40. Thus, attachment 20 is held by probe 10. Attachment section 40 also has injection port 48 for injecting an acoustic medium.

Membrane 50 which is formed of silicon rubber is arranged between reservoir section 30 and attachment section 40. As shown in FIGS. 7 and 8, the end portion of membrane 50 is adhered to flanges 65 and the inner periphery of seventh and eighth surfaces 44 and 45. The end portion of membrane 50 is urged against them by ring member 51. The central portion of membrane 50 defines acoustic lens 52. Acoustic lens 52 will be described later.

Reservoir section 30 and attachment section 40 are assembled as shown in FIG. 4. In reservoir section 30, the acoustic medium is held in space s defined by rectilinear member 35, contact membrane 36 and membrane 50. The acoustic medium is water or a colloidal material.

Figure 9:
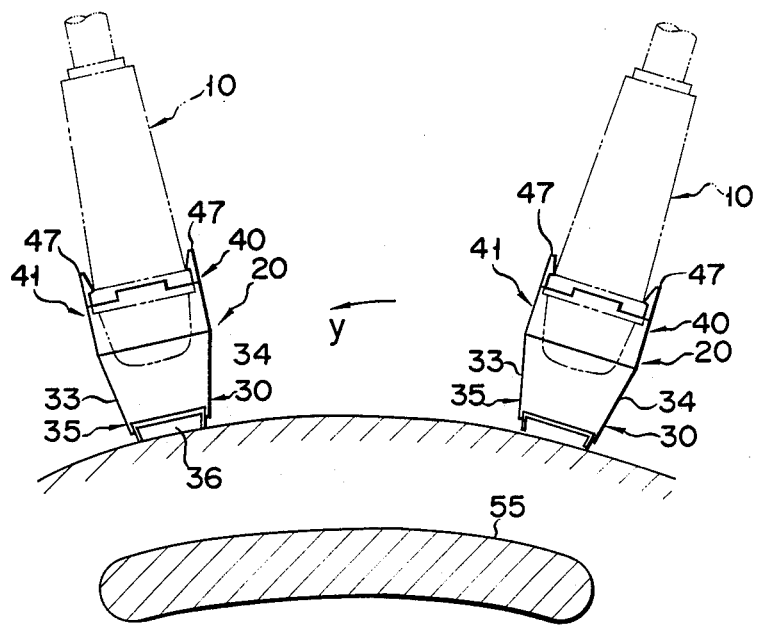
Figure 10:
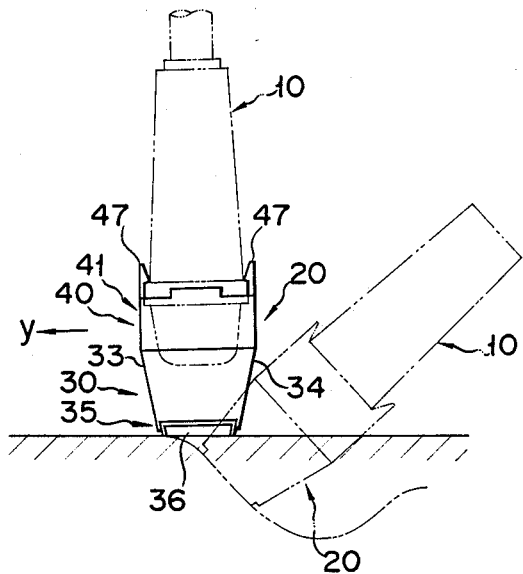

As described above, the distance between the lower edges of third and fourth surfaces 33 and 34 in the y direction is smaller than the distance between the upper edges thereof in the y direction. For this reason, the distance corresponding to a length of contact membrane 36 in the ±y directions becomes smaller than a conventional one. As shown in FIG. 9, when the operator moves probe 10 in the y direction, the frictional force between contact membrane 36 and the skin surface can be reduced as compared with the conventional attachment. Therefore, the operability of the attachment can be improved. As shown in FIG. 10, when contact membrane 36 is pivoted while being brought into contact with the skin surface (pivot scanning), attachment 20 can remain in satisfactory contact with the human body. For this reason, the contact between contact membrane 36 and the skin surface can be improved. Note that reference numeral 55 denotes an affected part.

As shown in FIG. 8, ultrasound beams radiated from transducer elements 11 are converged. Therefore, third and fourth surfaces 33 and 34 are located outside the convergence range of the ultrasound beams, so that the ultrasound beams will not be shielded by third and fourth surfaces 33 and 34. More specifically, when third and fourth surfaces 33 and 34 are respectively formed to be parallel to an imaginary plane on which the ultrasound beams are converged, the distance of contact membrane 36 in the y direction can be minimized.

Figure 1:
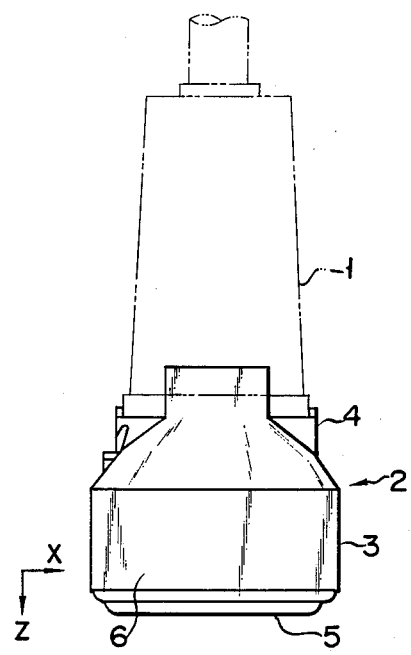
Figure 2:
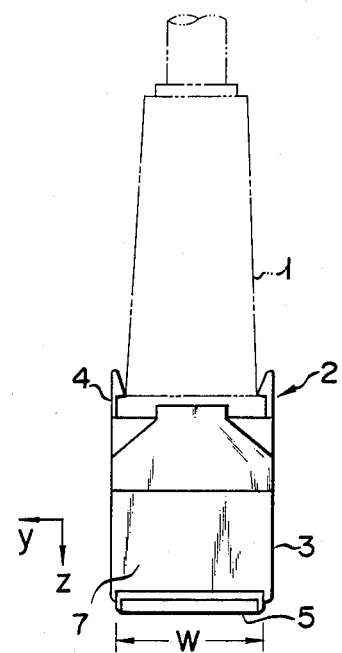
Figure 3:
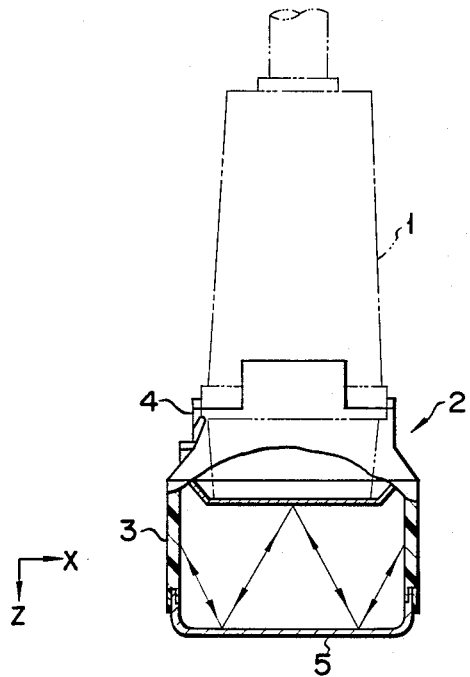

An advantage due to the fact that contact membrane 36 is convex will be explained below. The ultrasound beams radiated from transducer elements 11 are often reflected by the inner surface of contact membrane 36. Conventionally, as shown in FIG. 3, since the contact membrane is flat, the ultrasound beams are multiple-reflected by the inner surface of the side portion of the attachment, and are then received by the transducer elements. In this case, as shown in FIG. 11, a multiple-reflected image 53 is displayed on a cathode-ray tube, and a precise diagnosis (reading) is impeded. However, in this invention, as shown in FIG. 7, contact membrane 36 projects downward. Preferably, as indicated by two-dot chain line in FIG. 7, contact membrane 36 has a radius of curvature perpendicular to the radiated ultrasound beams. In this case, the ultrasound beams are reflected in the direction opposite to the irradiation direction on the basis of Snell's law. The transmittance of the ultrasound beams can be improved, and the sidewardly reflected ultrasound beams can be eliminated. For this reason, the ultrasound beams will not be multiple-reflected inside the attachment. Unlike in the conventional attachment, the multiple-reflected image cannot be displayed on the cathode-ray tube, and an accurate diagnosis (reading) will not be impeded. Therefore, as indicated by the solid line in FIG. 7, even if contact membrane 36 has a predetermined radius of curvature and convex the multiple-reflected image will not be displayed on the cathode-ray tube, and a precise diagnosis (reading) will not be disturbed. Since contact membrane 36 is convex, it can be brought into tight contact with a recess (e.g., a neck) in the body surface. For this reason, the contact between contact membrane 36 and the skin surface can be improved.

It is most preferable that first and second surfaces 31 and 32 are perpendicular to the x direction, as shown in FIG. 7. When the first and second surfaces are inclined outwardly, as indicated by the two-dot chain line in FIG. 7, the ultrasound beams can be free from multiple reflection. However, the operability of the attachment is degraded. When first and second surfaces 31 and 32 are inclined inwardly, artifacts can be removed from a region of interest (ROI). However, the ultrasound beams may be multiple-reflected. Therefore, it is most preferable that first and second surfaces 31 and 32 are perpendicular to the x direction.

Acoustic lens 52 formed on membrane 50 will be explained below. In order to observe an organ near the surface of the patient's skin (e.g., the thyroid gland or the carotid artery) with high image quality and in a wide field of view, focal point $P_1$ of the acoustic lens of the probe is preferably located near the skin surface, and preferably coincides with the ROI.

More specifically, when the attachment without the acoustic lens is attached to probe 10, focal point $P_1$ of acoustic lens 13 of probe 10 is located nearer the skin surface by the depth of water of the attachment than in a case wherein no attachment is attached. However, if the depth of water of the attachment falls outside the predetermined value, focal point $P_1$ does not often coincide with the ROI. For example, if the distance between acoustic lens 13 of probe 10 and focal point P1 of the lens is 6 cm, a depth of the ROI is 2 cm. If a depth of water of the attachment is 2 cm, focal point $P_1$ is located at a position separated from the skin surface by 4 cm. For this reason, the focal point is deviated from the ROI by 2 cm. In this case, the image of the ROI cannot be clearly displayed.

In this case, if the depth of water of the attachment is increased, the focal point can coincide with the ROI. However, if the depth of water of the attachment is increased, the operability of the attachment is degraded.

Figure 12:
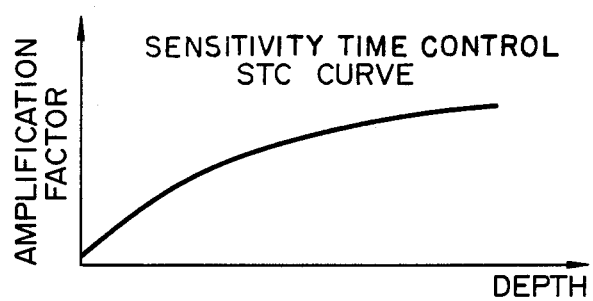
FIG. 12 is a graph showing an STC curve.

In addition, the deeper the observation region is, the weaker the ultrasound signals reflected from the region will be in a ultrasound diagnostic apparatus. Such being the case, the gain is compensated in accordance with a gain compensation curve (STC or Sensitivity time control curve) shown in FIG. 12. However, when the attachment is enlarged to increase the depth of water, the compensation operation will increase the gain more than needed, due to the fact that the strength of the ultrasound signals travelling through the water in the attachment will scarcely be decreased. As a result, multiple-reflection will occur at membrane 36, due to which artifacts appear on the cathode-ray tube, as shown by reference numerals 53 and 53 in FIG. 11.

When only the acoustic lens is attached without attaching the attachment onto the ultrasound probe, the probe comes too close to the ROI. In this case, as shown in FIG. 10, since the image of the ROI is displayed on sector upper position u, the field of view of the image scanning is narrowed.

In the attachment according to the present invention, as shown in FIG. 8, acoustic lens 52 is formed on membrane 50. Acoustic lens 52 has a projection shape when viewed from the x direction. The radius of curvature of the upper surface of acoustic lens 52 is equal to that of acoustic lens 13 provided to probe 10. The radius of curvature of the lower surface of acoustic lens 52 is smaller than that of the upper surface. A focal point when acoustic lenses 13 and 52 are used together corresponds to $P_2$. Thus, focal point $P_2$ is located nearer the skin surface than focal point $P_1$. For this reason, the the focal point and the ROI coincide with each other without increasing the depth of water of the attachment and without causing the probe and the ROI to come too close to each other. Accordingly, it is not necessary for the attachment to be enlarged in order to increase the depth of water, so that the gain does not have to be increased more than necessary. Thus, the artifacts do not appear on the cathode-ray tube.

Therefore, when various attachments having acoustic lenses with different focal lengths are used, various internal organs 55 (e.g., the thyroid gland and the carotid artery) which are near the skin surface can be observed with high image quality and with a wide field of view.

The present invention can also be applied to a linear scan probe.

What is claimed is:

1. An attachment device for attachment to a diagnostic ultrasonic probe of the type including a transducer means for radiating ultrasound beams in a scanning plane for scanning an organic body and for converting echoes produced in the scanned organic body and returned to the transducer means to electric signals for reconstructing a tomographic image of the scanned organic body, said attachment device comprising:

a housing for holding an acoustic medium for transmitting the ultrasound beams without attenuation, said housing including sidewall elements; a transmission section operatively coupled to said sidewall elements and permitting ultrasound beams to be transmitted therethrough, said transmission section including acoustic lens means for converging the ultrasound beams radiated from the transducer means to a predetermined point in the scanning plane; a contact membrane mounted to said sidewall elements and spaced from said transmission section, said contact membrane permitting ultrasound beams to be transmitted therethrough; an inner surface of said sidewall elements, the transmission section, and the contact membrane defining a chamber for receiving the acoustic medium; an outer surface of said contact membrane relative to said chamber being adapted to be brought into contact with a skin surface of the organic body; said contact membrane being mounted to said sidewall elements so as to have a cross-section in the scanning plane which is convex and defines a predetermined radius of curvature such that a majority of the ultrasound beams radiated from the transducer means of the probe and transmitted through the acoustic medium are transmitted through the contact membrane; and means for coupling the housing to the probe, said coupling means coupling the housing to the probe so that the transducer means is in facing relation to the transmission section of the housing and so that said scanning plane of the probe extends through the transmission section, the acoustic medium and the contact membrane when the attachment device is attached to the probe.

2. An attachment device according to claim 1, wherein said contact membrane is formed from a flexible material.

3. An attachment according to claim 2, wherein said sidewall elements include a pair of sidewalls which face each other and are disposed on either side of said scanning plane, the sidewalls of said pair each including a lower edge portion which abuts the contact membrane and is convexly curved in the direction of the scanning plane whereby the cross-section of the contact membrane in the scanning plane is maintained curved convexly from the chamber.

4. An attachment device as in claim 1, wherein the radius of curvature of said contact membrane is such that the ultrasound beams radiated from the transducer means impinge upon the contact membrane perpendicularly thereto.

5. An attachment device as in claim 1, wherein said transmission section is formed of a flexible membrane which permits ultrasound beams to be transmitted therethrough.

6. An attachment device according to claim 1, wherein the attachment device is for attachment to a probe which further includes an acoustic lens means for permitting the ultrasound beams radiated from the transducer means to be transmitted therethrough and for converging the transmitted ultrasound beams to a predetermined point in the scanning plane, the acoustic lens means of the probe including an acoustic lens, and wherein said acoustic lens means of said attachment device includes an inside surface which is adapted to be in contact with the acoustic medium within the chamber of the housing and an outside surface spaced from said acoustic medium a distance greater than the inside surface thereof, said acoustic lens means of the probe having an outside surface which is adapted to contact the outside surface of the acoustic lens means of the attachment device when the attachment device is coupled to the probe with the coupling means, and wherein a radius of curvature of the acoustic lens means of the attachment device is equal to a radius of curvature of an outside surface of the acoustic lens means of the probe and a radius of curvature of an inside surface of the acoustic lens means of the attachment device is shorter than the radius of curvature of the outside surface of the acoustic lens means of the probe.

7. An attachment device as in claim 1, wherein the attachment device is for attachment to a probe which further includes an engagement step and wherein said coupling means of the attachment device includes a hole into which the probe is fitted and inserted when the attachment device is attached to the probe and said coupling means further includes an engaging clip for engaging the engagement step of the probe.

* * * * *

UNITED STATES PATENT AND TRADEMARK OFFICE
CERTIFICATE OF CORRECTION

PATENT NO. : 4,867,169

DATED : September 19, 1989

INVENTOR(S) : MACHIDA et al.

It is certified that error appears in the above-identified patent and that said Letters Patent is hereby corrected as shown below:

ON THE FIRST, COVER PAGE:

Please insert the following: --[73] Assignee: Kabushiki Kaisha Toshiba, Kawasaki, Japan--

Signed and Sealed this

Sixteenth Day of October, 1990

*Attest:*

HARRY F. MANBECK, JR.

*Attesting Officer*     *Commissioner of Patents and Trademarks*